United States Patent
Bittner et al.

(10) Patent No.: US 9,470,872 B2
(45) Date of Patent: Oct. 18, 2016

(54) REFLECTIVE OPTICAL ELEMENT (71) Applicant: Carl Zeiss SMT GmbH, Oberkochen (DE)

(72) Inventors: Boris Bittner, Roth (DE); Norbert Wabra, Werneck (DE); Sonja Schneider, Oberkochen (DE); Ricarda Schneider, Zusmarshausen (DE); Hendrik Wagner, Aalen (DE); Rumen Iliew, Oberkochen (DE); Walter Pauls, Huettlingen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 121 days.

(21) Appl. No.: 14/528,690

(22) Filed: Oct. 30, 2014

(65) Prior Publication Data

US 2015/0116703 A1 Apr. 30, 2015

(30) Foreign Application Priority Data

Oct. 30, 2013 (DE) .................. 10 2013 222 140

(51) Int. Cl.
  *G03F 9/00* (2006.01)
  *G03F 1/52* (2012.01)
  *G02B 7/18* (2006.01)
  *G01N 21/95* (2006.01)
  *G03F 7/20* (2006.01)
  (Continued)

(52) U.S. Cl.
  CPC .............. *G02B 7/181* (2013.01); *G01N 21/95* (2013.01); *G03F 1/84* (2013.01); *G03F 7/702* (2013.01); *G03F 7/7095* (2013.01); *G03F 7/70316* (2013.01); *G03F 7/70891* (2013.01); *G21K 1/062* (2013.01); *G01N 2201/0636* (2013.01); *G21K 2201/067* (2013.01)

(58) Field of Classification Search
  CPC ..................................... G03F 9/00; G03F 1/52
  See application file for complete search history.

(56) References Cited

U.S. PATENT DOCUMENTS 7,623,620 B2   11/2009   Mann et al.
7,977,651 B2   7/2011    Mann et al.
(Continued)

FOREIGN PATENT DOCUMENTS

DE    19903807 A1    11/1999
DE    10220816 A1    11/2003
(Continued)

OTHER PUBLICATIONS

Noranzyk, A., Thermal Conductivity Measurements of Graphite Samples, Colorado School of Mines, Aug. 2009.
(Continued)

*Primary Examiner* — Stephen Rosasco
(74) *Attorney, Agent, or Firm* — Edell, Shapiro & Finnan, LLC (57) ABSTRACT A reflective optical element for a microlithographic projection exposure apparatus, a mask inspection apparatus or the like. The reflective optical element has an optically effective surface, an element substrate (12, 32, 42, 52), a reflection layer system (14, 34, 44, 54) and at least one deformation reduction layer (15, 35, 45, 55, 58). When the optically effective surface (11, 31, 41, 51) is irradiated with electromagnetic radiation, a maximum deformation level of the reflection layer system is reduced in comparison with a deformation level of an analogously constructed reflective optical element without the deformation reduction layer.

21 Claims, 5 Drawing Sheets (51) Int. Cl.
*G03F 1/84* (2012.01)
*G21K 1/06* (2006.01)

(56) References Cited

U.S. PATENT DOCUMENTS

| 2003/0162104 A1* | 8/2003 | Shoki | B82Y 10/00 430/5 |
| 2008/0266651 A1 | 10/2008 | Murakami et al. | |
| 2009/0316128 A1 | 12/2009 | Mann et al. | |
| 2012/0162755 A1 | 6/2012 | Stroessner et al. | |

FOREIGN PATENT DOCUMENTS

| DE | 10335982 A1 | 3/2005 |
| DE | 102009041405 A1 | 3/2011 |
| DE | 102012205181 A1 | 10/2013 |
| DE | 102012212757 A1 | 1/2014 |
| DE | 102012212898 A1 | 1/2014 |
| WO | 2013143666 A1 | 10/2013 |
| WO | 2014012660 A2 | 1/2014 |
| WO | 2014016168 A1 | 1/2014 |
| WO | 2014139543 A1 | 9/2014 |

OTHER PUBLICATIONS

Office Action in corresponding German Application No. 10 2013 222 140.1, dated Mar. 13, 2014, along with an English translation.
Debuysser, Klaartje et al., "ZrO2—ZrW2O8 Composites with tailor-made Thermal Expansion", Paper Ceramics-Silikaty 48, (4) pp. 139-144, paper presented at the conference Solid State Chemisrty 2004, Prague, Sep. 13-17, 2004.

* cited by examiner

REFLECTIVE OPTICAL ELEMENT

CROSS-REFERENCE TO RELATED APPLICATIONS

The following disclosure is based on and claims the benefit, under 35 U.S.C. §119(a), of German Patent Application No. 10 2013 222 140.1, filed on Oct. 30, 2013, which German Patent Application is incorporated in its entirety into the present application by reference.

FIELD OF AND BACKGROUND OF THE INVENTION

The invention relates to a reflective optical element, in particular for a microlithographic projection exposure apparatus or for a mask inspection apparatus.

Microlithography is used for producing microstructured components, such as, for example, integrated circuits or LCDs. The microlithography process is carried out in a so-called projection exposure apparatus having an illumination device and a projection lens. The image of a mask (=reticle) illuminated with the illumination device is in this case projected by the projection lens onto a substrate (e.g. a silicon wafer) coated with a light-sensitive layer (photoresist) and arranged in the image plane of the projection lens, in order to transfer the mask structure to the light-sensitive coating of the substrate.

Mask inspection apparatuses are used for inspecting reticles for microlithographic projection exposure apparatuses.

In projection lenses or inspection lenses designed for the EUV range, i.e. at wavelengths of e.g. approximately 13 nm or approximately 7 nm, owing to the lack of availability of suitable light-transmissive refractive materials, reflective optical elements are used as optical components for the imaging process.

One problem that occurs in practice is that reflective optical elements designed for operation in the EUV, in particular owing to the absorption of the radiation emitted by the EUV light source, experience heating and an accompanying thermal expansion or deformation, which can in turn result in an impairment of the imaging properties of the optical system. This is the case particularly if use is made of illumination settings having comparatively small illumination poles (e.g. in dipole or quadrupole illumination settings), in which the element heating or deformation varies greatly across the optically effective surface of the reflective optical element.

Transferring solution approaches known for VUV lithography systems (having an operating wavelength e.g. of approximately 200 nm or approximately 160 nm) for overcoming the above-described problem of element heating to EUV systems has proven difficult. This is so in part because the number of optically effective surfaces available for active deformation compensation is, relative to VUV systems, greatly limited owing to the comparatively smaller number of optical elements or mirrors that are used in EUV lithography. (The number of elements or mirrors is kept small in order to avoid excessively high light losses on account of the necessary reflections).

In order to overcome the above-described problem of element heating in EUV systems it is known, in particular, to use additional devices for realizing rigid-body movements and/or temperature changes in the region of the optically effective surface of the reflective optical elements designed for operation in the EUV. Such solutions, however, increase the complexity of the systems.

OBJECTS AND SUMMARY OF THE INVENTION

It is an object of the present invention to provide a reflective optical element, in particular for a microlithographic projection exposure apparatus or for a mask inspection apparatus, which, in conjunction with comparatively little structural complexity, enables an effective avoidance or at least a reduction of thermal deformations or accompanying impairments of the imaging behaviour.

A reflective optical element, in particular for a microlithographic projection exposure apparatus or for a mask inspection apparatus and addressing the above object, comprises, according to one formulation:

an optically effective surface,
an element substrate,
a reflection layer system, and
at least one deformation reduction layer which, upon the optically effective surface being irradiated with electromagnetic radiation, reduces a maximum deformation level of the reflection layer system in comparison with an analogous construction without the deformation reduction layer.

The inventors have recognized that the maximum deformation level can be reduced by virtue of the fact that, in the case of the reflective optical element according to the invention, a deformation reduction layer is taken into account or incorporated from the outset and has the effect that an undesired thermally governed deformation of the reflective optical element toward the vacuum as far as possible does not actually occur in the first place. This deformation level can be defined here in each case in the direction of the normal vector of the element surface. If even pronounced aspheres are present, the deformation level can preferably be defined by the element surface being approximated by a spherical radius (as "basic radius"), onto which the respective asphere is modulated, the deformation level then being defined as deformation in the direction of the normal vector to the spherical surface described by said radius.

In other words, the present invention includes, in particular, the concept of suitably incorporating a deformation reduction layer so as already to prevent thermally governed deformations from the outset and thus to render unnecessary or at least considerably simplify an active deformation compensation through rigid-body movements and/or temperature changes in the region of the optically effective surface.

In accordance with one embodiment, the reflection layer system has at least one layer composed of a first material having a first coefficient of thermal expansion, and the at least one deformation reduction layer has a second material having a second coefficient of thermal expansion, wherein the first and second coefficient of thermal expansions have opposite signs.

In accordance with this approach, as will be explained in even greater detail below, a thermally governed volume expansion of the reflection layer system during operation of the reflective optical element or of the optical system having the latter can be compensated for by an opposite volume contraction of the deformation reduction layer, said volume contraction ideally being of equal size in terms of absolute value, with the consequence that the effective volume change of the arrangement comprising reflection layer system, on the one hand, and deformation reduction layer, on the other hand, that results from the heating of the optically effective surface is reduced to almost zero. As a result, with optimum coordination of reflection layer system, on the one hand, and deformation reduction layer, on the other hand, in particular with regard to the respective layer thicknesses and materials, it is thus possible to achieve to a certain extent an intrinsic and self-consistent deformation compensation in the reflective optical element itself.

In accordance with one embodiment, the first material comprises zirconium (Zr), yttrium (Y), molybdenum (Mo), niobium (Nb), silicon (Si), germanium (Ge), rhodium (Rh), ruthenium (Ru), ruthenium dioxide ($RuO_2$) or ruthenium-silicon (RuSi).

In accordance with one embodiment, the second material is selected from the group containing $ZrMo_2O_8$, $ZrW_2O_8$, $HfMo_2O_8$, $HfW_2O_8$, $Zr_2(MoO_4)_3$, $Zr_2(WO_4)_3$, $Hf_2(MoO_4)_3$, $Hf_2(WO_4)_3$, $SCF_3$, $ZnC_2N_2$, $ZnF_2$, $Y_2W_3O_{12}$ and $BiNiO_3$. Preferably, the second material used is an isotropic material such as e.g. a cubically crystalline or amorphous material (for avoiding mechanical stresses and resultant microcracks) having a comparatively high negative coefficient of thermal expansion and good thermodynamic stability.

In accordance with one embodiment, the effective volume change $\Delta V_{eff}$ of the arrangement comprising reflection layer system and deformation reduction layer that results from a heating of the optically effective surface by a predetermined temperature difference is a maximum of 90%, in particular a maximum of 50%, more particularly a maximum of 10%, of the volume change $V_1$ of the reflection layer system that results from said heating. In this case, this condition can be met in particular for a heating of the optically effective surface by a temperature difference of at least 1K, in particular at least 5K, more particularly at least 10K.

In accordance with one embodiment, the at least one deformation reduction layer has a heat distribution layer having an increased thermal conductivity in comparison with the element substrate. This heat distribution layer can have in particular a thermal conductivity of at least 100 W/mK. The heat distribution layer can furthermore comprise in particular at least one material selected from the group containing graphite, aluminium (Al), silver (Ag), gold (Au), copper (Cu) and $ZrW_2O_8$.

What can be achieved in accordance with this approach, as will be explained in even greater detail below, is that the heat propagating within the reflective optical element upon electromagnetic radiation impinging on the optically effective surface is distributed better in a lateral direction (i.e. direction perpendicular to the light propagation direction or optical system axis), that is to say that a corresponding temperature distribution within the reflective optical element is "spread" with the consequence that undesired pronounced local deformations in particular in the region of the element substrate—which generally has only poor thermal conductivity—are avoided or at least greatly reduced. Particularly in the case of illumination settings having relatively small illumination poles (e.g. in dipole or quadrupole illumination settings), the heat distribution or deformation can thus be distributed uniformly over the optically effective surface of the reflective optical element before entry into the element substrate.

In accordance with one embodiment, a heat insulation layer for delaying the entry of heat into the element substrate is arranged between the reflection layer system and the deformation reduction layer. This heat insulation layer can comprise quartz, in particular.

In accordance with one embodiment, a further intermediate layer for avoiding the transfer of surface roughnesses to the reflection layer system is furthermore arranged between the reflection layer system and the deformation reduction layer. This intermediate layer can comprise quartz, in particular.

In accordance with one embodiment, the reflective optical element is designed for an operating wavelength of less than 30 nm, in particular less than 15 nm. However, the invention is not restricted thereto, such that in further applications the invention can also be realized advantageously in an optical system having an operating wavelength in the VUV range (e.g. of less than 200 nm or less than 160 nm).

The reflective optical element according to the invention can be a mirror, in particular a mirror for a microlithographic projection exposure apparatus or a mirror for a mask inspection apparatus. Furthermore, the reflective optical element according to the invention can also be a reticle for a microlithographic projection exposure apparatus.

The invention furthermore relates to an optical system of a microlithographic projection exposure apparatus, in particular an illumination device or a projection lens, an optical system of a mask inspection apparatus, and also a microlithographic projection exposure apparatus and a mask inspection apparatus comprising at least one reflective optical element having the features described above.

Further configurations of the invention can be gathered from the description and the dependent claims.

BRIEF DESCRIPTION OF THE DRAWINGS

The invention is explained in greater detail below on the basis of exemplary embodiments illustrated in the accompanying drawings.

In the figures:

FIG. 3B shows a schematic illustration for elucidating the mode of action of the construction according to the invention from FIG. 3a;

DETAILED DESCRIPTION

Figure 1:
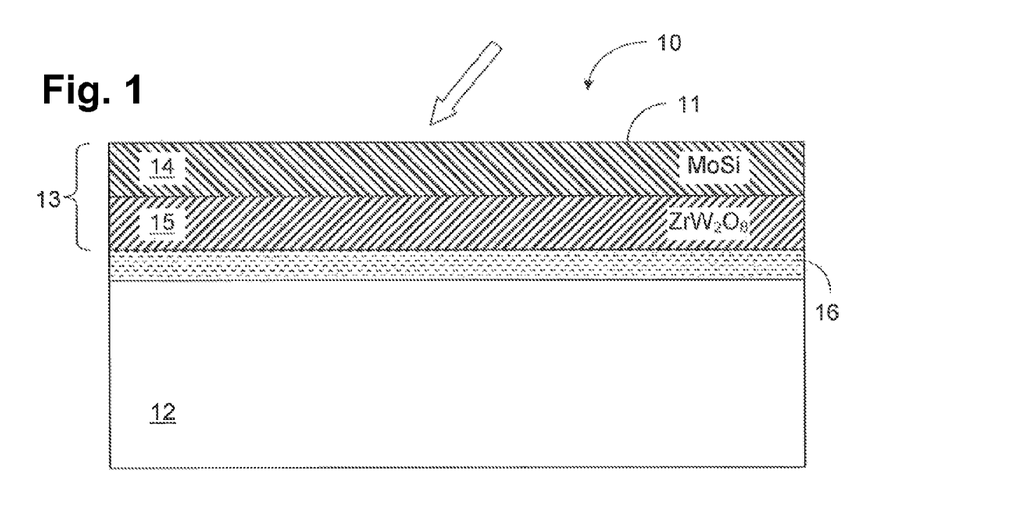
FIG. 1 shows a schematic illustration for elucidating the construction of a reflective optical element in accordance with a first embodiment of the invention.

FIG. 1 shows a schematic illustration for explaining the construction of a reflective optical element according to the invention in a first embodiment of the invention. The reflective optical element 10 comprises in particular an element substrate 12 produced from an arbitrary suitable (mirror) substrate material. Suitable element substrate materials are e.g. titanium dioxide ($TiO_2$)-doped quartz glass, wherein merely by way of an exemplary embodiment and without the invention being restricted thereto, the materials sold under the trademarks ULE® (from Corning Inc.) or Zerodur® (from Schott AG) can be used.

Furthermore, the reflective optical element 10 has a reflection layer system 14 in a manner known per se in principle, said reflective optical element, in the embodiment illustrated, comprising merely by way of example a molybdenum-silicon (Mo—Si) layer stack. Without the invention being restricted to specific configurations of said layer stack, a merely exemplary suitable construction can comprise 50 plies or layer packets of a layer system comprising molybdenum (Mo) layers having a layer thickness of 2.4 nm in each case and silicon (Si) layers having a layer thickness of 3.3 nm in each case. Optionally, provision can also be made of further functional layers such as, for example, a capping layer ("cap layer"), which can consist e.g. of Ru, Rh, SiC, C, Ir, Mo$_2$C, Y$_2$O$_3$ or Si$_3$N$_4$, a substrate protection layer (SPL), which can consist e.g. of compounds comprising at least one of the elements Pt, Cu, Co, Sn, Ni and Ag, and/or diffusion barriers, which can consist for example of C, B$_4$C, Si$_x$N$_y$, SiC, Mo$_2$C, MoSi$_2$, Y$_5$Si$_3$ or Nb$_4$Si.

Figure 2A:
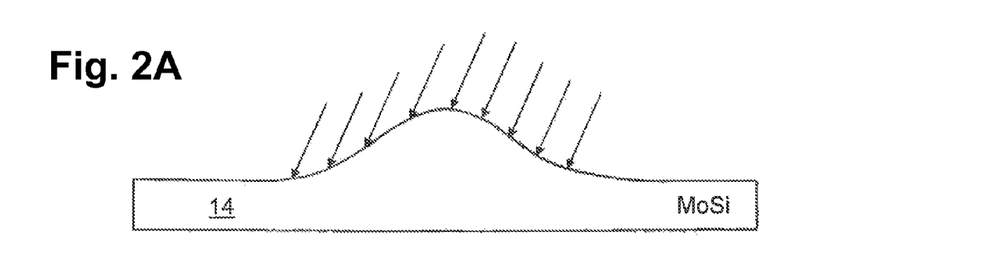
FIGS. 2A-D show schematic illustrations or diagrams for elucidating the mode of action of the construction according to the invention from FIG. 1.
Figure 2B:
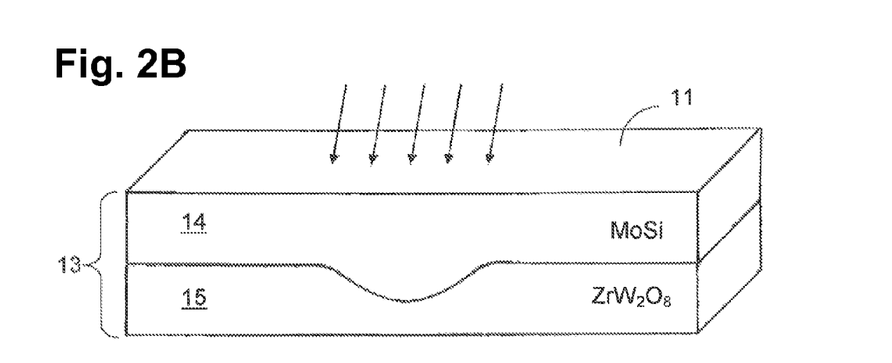

The reflective optical element 10 can be, in particular, a reflective optical element designed for operation in the EUV or a mirror of an optical system, in particular of the projection lens or of the illumination device of a microlithographic projection exposure apparatus or of the inspection lens of a mask inspection apparatus. The impingement of electromagnetic EUV radiation (indicated by an arrow in FIG. 1) on the optically effective surface 11 of the reflective optical element 10 during operation of the optical system has the consequence of a volume expansion of the reflection layer system 14 on account of the positive coefficient of thermal expansion of the material of the reflection layer system 14 (an average coefficient of thermal expansion of approximately $3.61 \cdot 10^{-6}$ K$^{-1}$ results in the case of an MoSi layer stack). Depending of the intensity distribution of the incident electromagnetic radiation (that is to say, in particular depending on the set illumination setting in the case of a near-pupil reflective optical element), said volume expansion proceeds inhomogeneously over the optically effective surface 11, which is illustrated in a greatly simplified and schematic manner in FIG. 2A.

In order, then, at least partly to reduce the deformation of the reflective optical element 10 overall and in particular of the optically effective surface 11 thereof, this deformation being caused by the irradiation of the optically effective surface 11 with electromagnetic radiation, the reflective optical element 10 has a deformation reduction layer 15, which, in accordance with FIGS. 1-2 is situated on that side of the reflection layer system 14 which faces away from the optically effective surface 11. In the exemplary embodiment in FIG. 1, said deformation reduction layer 15 is constituted such that the deformation of the deformation reduction layer 15 caused by the impingement of electromagnetic radiation or the accompanying temperature increase proceeds precisely oppositely to the deformation of the reflection layer system 14.

For this purpose, the deformation reduction layer 15 has a coefficient of thermal expansion having an opposite sign in comparison with the material of the reflection layer system 14, that is to say a negative coefficient of thermal expansion in the exemplary embodiment. Merely by way of example (and without the invention being restricted thereto), the deformation reduction layer can be produced e.g. from ZrW$_2$O$_8$ having a thickness of 118 nm (wherein ZrW$_2$O$_8$ is a crystal material having a cubic crystal structure and a coefficient of thermal expansion of $-8.7 \cdot 10^{-6}$ K$^{-1}$ in the temperature range of 20K to 430K). In the abovementioned example (50 plies or layer packets of a layer system comprising Mo layers having a layer thickness of 2.4 nm and Si layers having a layer thickness of 3.3 nm), the resulting total thicknesses of 120 nm molybdenum (Mo) and 165 nm silicon (Si) can be compensated for by a 118 nm thick layer of ZrW$_2$O$_8$ with regard to the thermally governed deformation. In further embodiments, a layer of ZrW$_2$O$_8$ having a larger thickness can also be used in order additionally to compensate for the thermal expansion in the element substrate material (e.g. TiO$_2$-doped quartz glass).

Further suitable materials having a negative coefficient of thermal expansion are listed in Table 1:

TABLE 1

| Material | Coefficient of thermal expansion [$10^{-6}$ K$^{-1}$] |
|---|---|
| PbTiO$_3$ | −3.3 |
| Sc$_2$W$_3$O$_{12}$ | −2.2 |
| Y$_2$W$_3$O$_{12}$ | −4.2 |
| Lu$_2$W$_3$O$_{12}$ | −6.8 |
| NbOPO$_4$ | −3.7 |
| ZrV$_2$O$_7$ | −7.1 |
| ZrW$_2$O$_8$ | −8.7 |
| ZrMo$_2$O$_8$ | −5.0 |
| K$_5$Zr(PO$_4$)$_3$ | −0.5 |
| KZr$_2$(PO$_4$)$_3$ | −1.7 |
| Zn(CN)$_2$ | −18.1 |

Since the coefficient of thermal expansion itself is a function of temperature, in the case of an isotropic material (in particular having a negative coefficient of thermal expansion), the expansion or contraction can be assumed to be linear with temperature only for a limited temperature range. In order likewise to correct quadratic portions and higher-order portions, a plurality of suitable materials can also be mixed or stacked one above another in the layer construction. Furthermore, a deformation reduction layer 15 e.g. composed of ZrW$_2$O$_8$ (which e.g. with a thickness of 150 nm absorbs approximately 94% of EUV light having a wavelength of 13.5 nm) is preferably arranged as the bottommost layer (apart from a heat insulation layer and/or a substrate protection layer possibly present, as described further below) in the layer stack relative to the optically effective surface.

In practice, materials, layer thicknesses and layer sequences of the reflection layer system 14, on the one hand, and of the deformation reduction layer 15, on the other hand, can in each case be coordinated with one another or optimized such that an at least almost complete mutual compensation of the temperature-governed deformation is obtained. This effect is illustrated only schematically and in a greatly simplified manner in FIG. 2B. The volume expansion of the reflection layer system 14, which takes place primarily in the region of high radiation intensities or illumination poles, is compensated for in accordance with FIG. 2B by an opposite volume contraction of the deformation reduction layer 15, said volume contraction ideally being of the same size in terms of absolute value, with the consequence that the effective volume change of the arrangement 13 comprising reflection layer system 14 and deformation reduction layer 15 that results from the heating of the optically effective surface 11 is reduced to almost zero. Furthermore, as already mentioned, it is also possible at least partly to compensate for the thermal expansion in the element substrate material (e.g. in the TiO$_2$-doped quartz glass).

As a suitable criterion for quantitatively describing the reduction according to the invention of the temperature-governed deformation, it is possible to specify in particular an upper limit for the effective volume change $\Delta V_{\mathit{eff}}$ of the arrangement 13 comprising reflection layer system 14 and deformation reduction layer 15 that results from the heating by a predefined temperature difference. In this case, what can be achieved in particular by suitable coordination of materials and layer thicknesses of the reflection layer system 14, on the one hand, and of the deformation reduction layer 15, on the other hand, is that said resulting effective volume change $\Delta V_{\mathit{eff}}$ is a maximum of 90%, in particular a maximum of 50%, more particularly a maximum of 10%, of the volume change of the reflection layer system 14 itself that results from said heating.

Figure 2C:
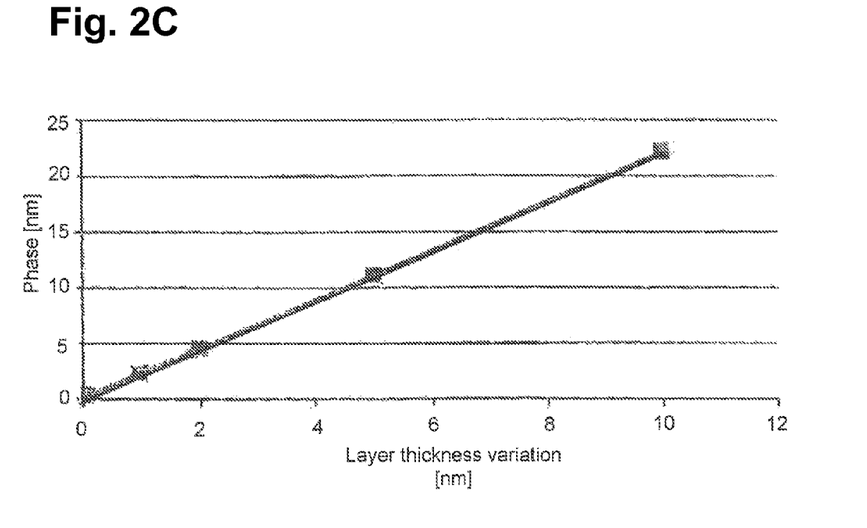

In accordance with FIG. 2C, in the case of a reflective optical element without a deformation reduction layer, a layer thickness variation of, for example, 2 nm or of 4 nm or of 5 nm (x-axis) is brought about owing to element heating. An unwanted local phase change of the wavefront of approximately 4 nm or of approximately 8 nm or of approximately 10 nm (y-axis) is brought about as a result. In the case of a reflective optical element having a deformation reduction layer designed according to the invention, no or only a negligible wavefront change takes place.

Figure 2D:
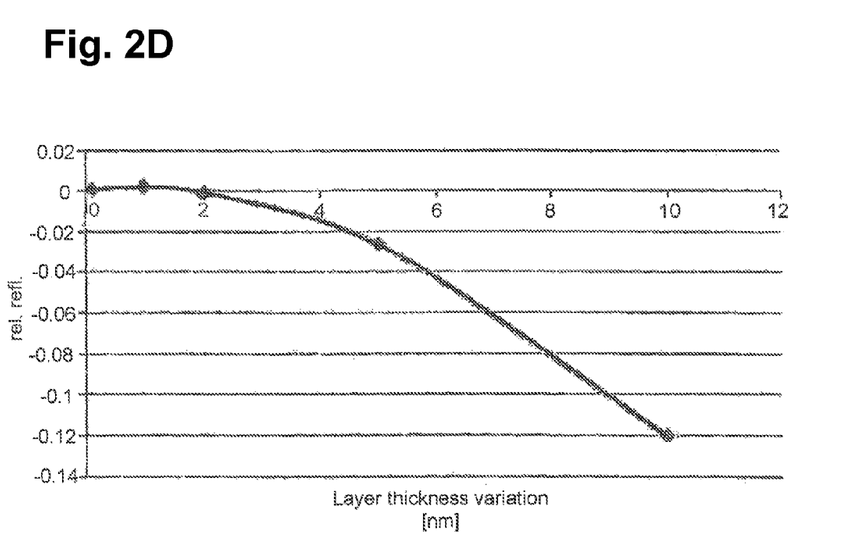

A variation of the reflectivity takes place both in the case of a reflective optical element without a deformation reduction layer and in the case of a reflective optical element with a deformation reduction layer. FIG. 2D shows by way of example for an EUV narrowband layer stack in the case of a layer thickness variation of 2 nm or of 4 nm or of 5 nm an unwanted local reflection reduction by approximately 0.1% or 1.6% or 2.5%, respectively. In the case of an EUV broadband layer stack, the contributions to an unwanted local layer thickness variation may be smaller. Currently expected local layer thickness variations caused by element heating are less than 5 nm, in particular less than 2 nm.

In accordance with FIG. 1, a heat insulation layer 16 for delaying the entry of heat into the element substrate 12 is furthermore also arranged between the arrangement 13 comprising reflection layer system 14 and deformation reduction layer 15 and the element substrate 12, wherein said heat insulation layer 16 e.g. composed of quartz having a coefficient of thermal expansion of approximately $0.5 \cdot 10^{-6}$ $K^{-1}$ and a thermal conductivity of approximately 1.38 W/mK (which is comparatively low for instance relative to copper with a value of 400 W/mK, or silicon with a value of 150 W/mK) can be vapour-deposited.

A further possible configuration of the deformation reduction layer according to the invention is explained below with reference to FIGS. 3A-B, wherein in comparison with FIG. 1 analogous or substantially functionally identical components are designated by reference numerals increased by 20.

Figure 3A:
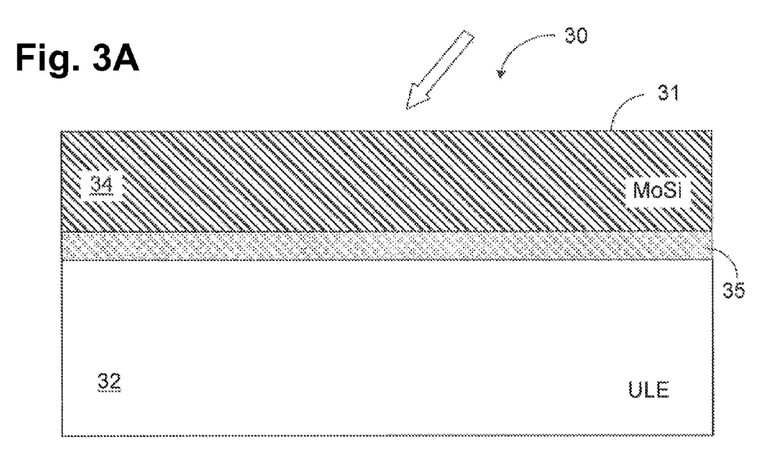
FIG. 3A shows a schematic illustration for elucidating the construction of a reflective optical element in accordance with a further embodiment of the invention.
Figure 3B:
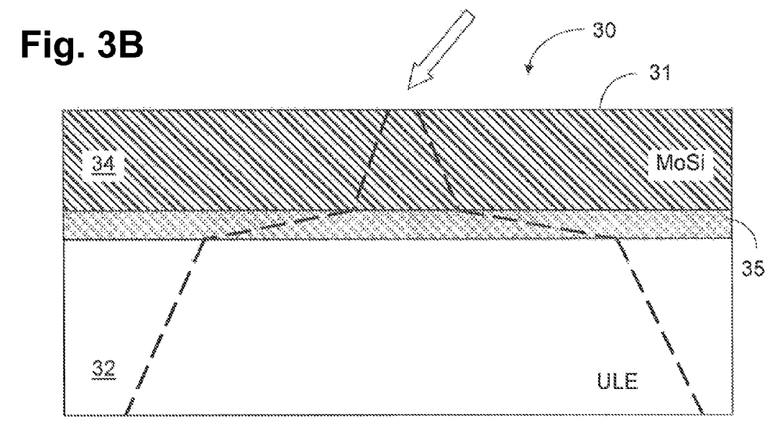

The reflective optical element 30 illustrated schematically in FIGS. 3A-B has, analogously to the reflective optical element 10 from FIG. 1, a deformation reduction layer 35 on that side of the reflection layer system 34 which faces away from the optically effective surface 31. In contrast to the embodiment from FIG. 1, however, the mode of action of the deformation reduction layer 35 in accordance with FIGS. 3A-B is based on the fact that the heat propagating within the reflective optical element 30 upon electromagnetic radiation impinging on the optically effective surface 31 is distributed better in particular in a lateral direction (i.e. direction perpendicular to the light propagation direction or optical system axis) (that is to say that a corresponding temperature distribution within the reflective optical element 30 is "spread").

This effect of a deformation reduction layer 35 configured as a "heat distribution layer" in the above sense is indicated once again merely in a greatly simplified manner in FIG. 3B and has the consequence that undesired pronounced local deformations in particular in the region of the element substrate 32 (which otherwise are caused by the comparatively poor thermal conductivity and a comparatively great temperature dependence of the coefficient of thermal expansion of the element substrate material such as e.g. ULE®) are avoided or at least greatly reduced.

Exemplary suitable materials for the heat distribution layer or deformation reduction layer 35 are for example graphite (having a thermal conductivity of approximately 130 W/mK, and a coefficient of thermal expansion of approximately $6.5 \cdot 10^{-6}$ $K^{-1}$), or copper (having a thermal conductivity of approximately 390 W/mK and a coefficient of thermal expansion of approximately $16 \cdot 10^{-6}$ $K^{-1}$).

The approach described above with reference to FIGS. 3A-B, thus takes account of the fact that particularly upon the setting of illumination settings having comparatively small illumination poles or greatly inhomogeneous intensity distributions on the optically effective surface of an e.g. near-pupil reflective optical element, comparatively high temperature gradients occur in the element substrate material since said element substrate material typically has only a low thermal conductivity and, moreover, a coefficient of thermal expansion greatly dependent on the respective temperature range. Resultant local deformations in the region of the element substrate in turn typically result in medium- to high-frequency optical aberrations in the lithographic process, which can be significantly reduced by the above-described approach of lateral heat distribution (or "spreading" of the location-dependent temperature distribution within the reflective optical element).

Figure 4:
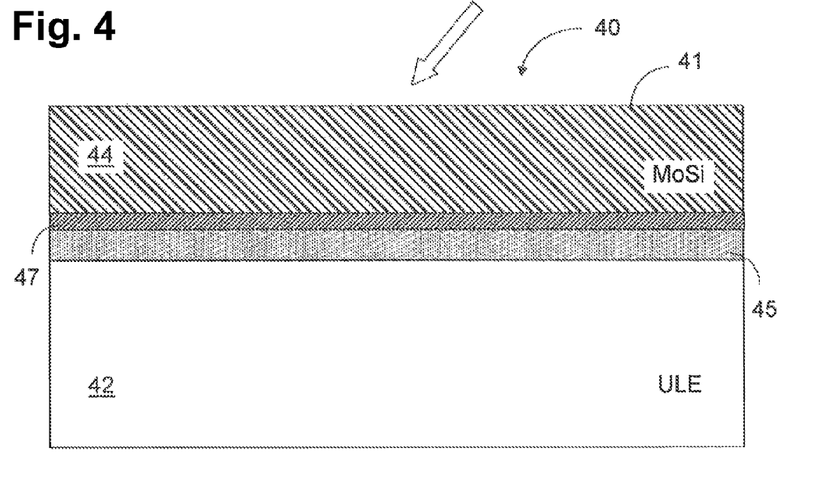
FIGS. 4-5 show schematic illustrations for elucidating the construction of a reflective optical element in accordance with further embodiments of the invention.

In accordance with FIG. 4, a smoothing layer as a further intermediate layer 47 for avoiding the transfer of surface roughnesses to the reflection layer system 44 can furthermore be arranged between the reflection layer system 44 and the deformation reduction layer 45. This smoothing layer can comprise quartz and/or silicon, for example. It may be necessary that the smoothing layer must be smoothed in a separate work operation after application. This smoothing can be effected for example by mechanical processing and/or by ion beam figuring.

Figure 5:
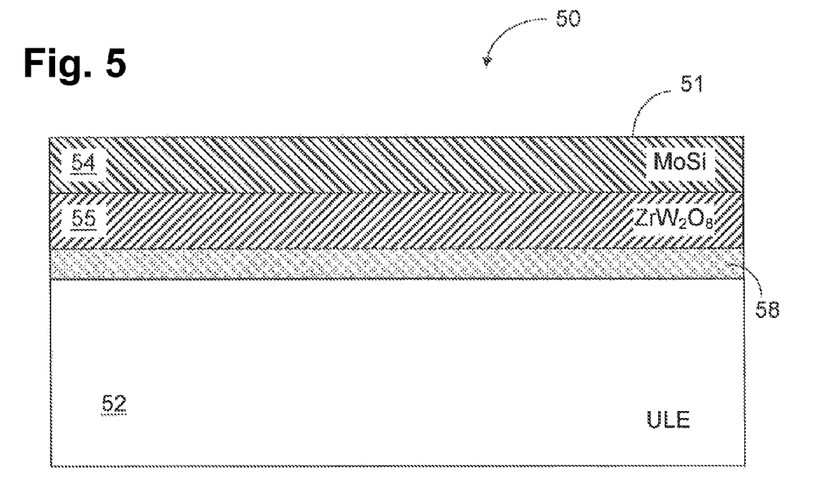

In further embodiments of the invention, the above-described approach of using at least one heat distribution layer as deformation reduction layer 35 can also be combined with the approach described above with reference to FIG. 1, as is illustrated merely schematically in FIG. 5. In this regard, both at least one deformation reduction layer 58 acting as heat distribution layer and at least one deformation reduction layer 55 having an opposite coefficient of thermal expansion in comparison with the reflection layer system 54 can also be used for the deformation reduction according to the invention.

In further embodiments, a layer stack having an alternating layer sequence composed of deformation reduction layers 55 and 58 can also be provided, wherein it is possible to produce the deformation reduction layer 55 as heat distribution layer in the above-described sense e.g. composed of graphite (e.g. having in each case a thickness of approximately 0.1338 μm) and the deformation reduction layer e.g. composed of $ZrW_2O_8$ (e.g. having a thickness of 0.1 μm) as layer material having opposite coefficient of thermal expansions in comparison with the material of the reflection layer system. Such a double-ply system can also be repeated multiply in a corresponding layer stack, wherein the abovementioned thicknesses can also be multiplied by an arbitrary factor (e.g. the factor 10 or 0.1). In this case, the thermal conductivity of the $ZrW_2O_8$, with a value of approximately 2 W/mK, is not significantly greater than that of ULE® (as exemplary element substrate material), but $ZrW_2O_8$, as described above, has a negative coefficient of thermal expansion of approximately $-8.7 \cdot 10^{-6}$ $K^{-1}$.

When designing the layer thicknesses of the compensation layers, it should be taken into consideration that a spreading of the local region to be compensated takes place via the heat distribution layers.

In a further exemplary embodiment, it is also possible in each case for a ply $ZrW_2O_8$ having the thickness $d_1$ to be supplemented by a ply composed of copper (Cu) having the thickness $d_2$, wherein $d_2 = 0.5438 \cdot d_1$ holds true, wherein such a double-ply system can likewise be repeated multiply in the layer construction.

Figure 6:
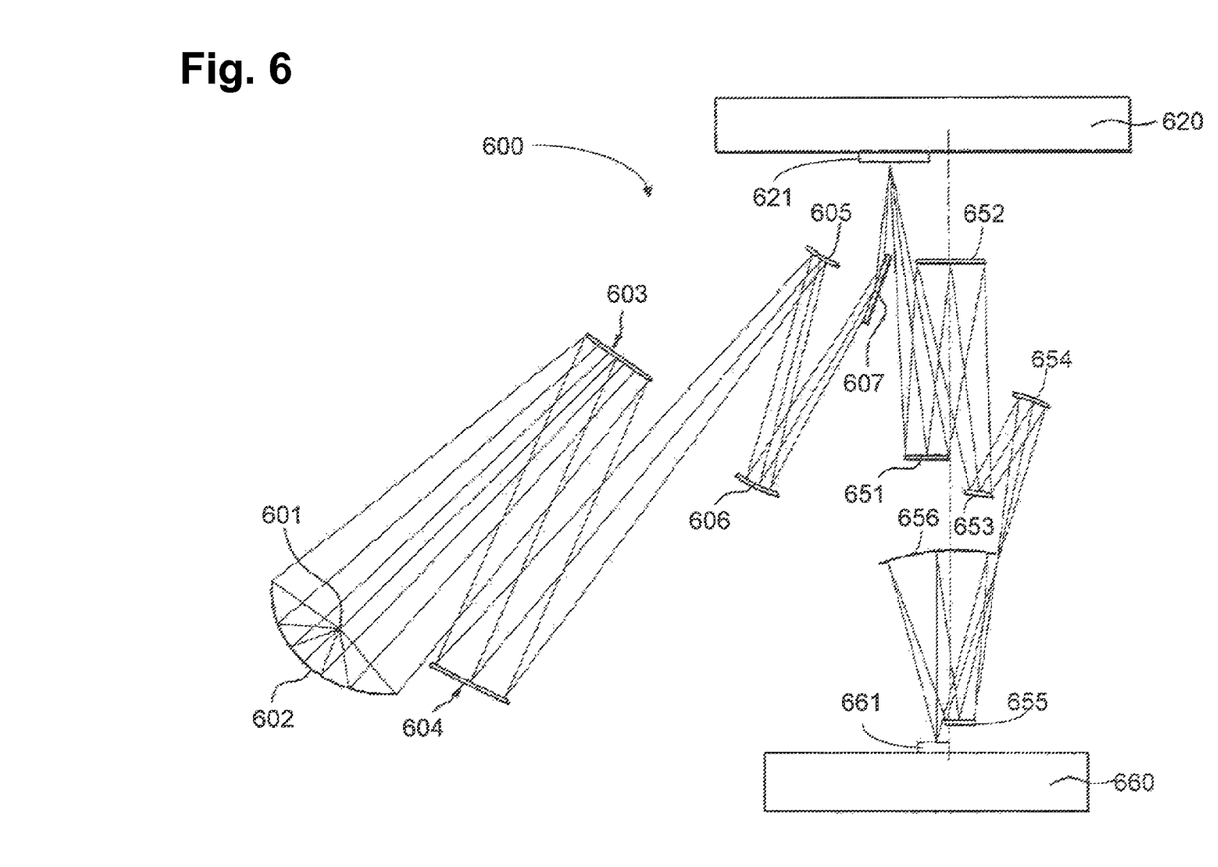
FIG. 6 shows a schematic illustration for elucidating the possible construction of a microlithographic projection exposure apparatus designed for operation in the EUV.

FIG. 6 shows a schematic illustration of an exemplary projection exposure apparatus which is designed for operation in the EUV and in which the present invention can be realized. In accordance with FIG. 6, an illumination device in a projection exposure apparatus 600 designed for EUV has a field facet mirror 603 and a pupil facet mirror 604. The light from a light source unit comprising a plasma light source 601 and a collector mirror 602 is directed onto the field facet mirror 603. A first telescope mirror 605 and a second telescope mirror 606 are arranged in the light path downstream of the pupil facet mirror 604. A deflection mirror 607 is arranged downstream in the light path and directs the radiation incident on it onto an object field in the object plane of a projection lens comprising six mirrors 651-656. A reflective structure-bearing mask 621 on a mask stage 620 is arranged at the location of the object field and is imaged with the aid of the projection lens into an image plane in which a substrate 661 coated with a light-sensitive layer (photoresist) is situated on a wafer stage 660.

Of the mirrors 651-656 of the projection lens, in particular the mirrors 651 and 652—arranged in the initial region of the projection lens relative to the optical beam path—can be configured in the manner according to the invention since the effect achieved according to the invention is then particularly pronounced owing to the summed reflection losses that are still comparatively low at these mirrors 651 and 652 and thus the relatively high light intensities. However, the invention is not restricted to application to the mirrors 651 and 652, such that in principle other mirrors can also be configured in the manner according to the invention.

Even though the invention has been described on the basis of specific embodiments, numerous variations and alternative embodiments are apparent to the person skilled in the art, e.g. by combination and/or exchange of features of individual embodiments. Accordingly, for the person skilled in the art, such variations and alternative embodiments are concomitantly encompassed by the present invention, and the scope of the invention is restricted only within the meaning of the appended patent claims and the equivalents thereof.

The invention claimed is:

1. Reflective optical element having an optically effective surface and comprising:
an element substrate;
a reflection layer system;
at least one deformation reduction layer which, upon the optically effective surface being irradiated with electromagnetic radiation, reduces a maximum deformation level of the reflection layer system in comparison with an analogous construction of a reflective optical element without the deformation reduction layer; and
an intermediate layer arranged between the reflection layer system and the deformation reduction layer and configured to block transfer of surface roughnesses to the reflection layer system,
wherein the reflection layer system comprises at least one layer composed of a first material having a first coefficient of thermal expansion, and the at least one deformation reduction layer comprises a second material having a second coefficient of thermal expansion, and wherein the first and the second coefficients of thermal expansions have mutually opposite signs.

2. Reflective optical element according to claim 1, wherein the first material comprises at least one of zirconium (Zr), yttrium (Y), molybdenum (Mo), niobium (Nb), silicon (Si), germanium (Ge), rhodium (Rh), ruthenium (Ru), ruthenium dioxide ($RuO_2$) and ruthenium-silicon (RuSi).

3. Reflective optical element according to claim 1, wherein the second material is selected from the group consisting essentially of $ZrMo_2O_8$, $ZrW_2O_8$, $HfMo_2O_8$, $HfW_2O_8$, $Zr_2(MoO_4)_3$, $Zr_2(WO_4)_3$, $Hf_2(MoO_4)_3$, $Hf_2(WO_4)_3$, $ScF_3$, $ZnC_2N_2$, $ZnF_2$, $Y_2W_3O_{12}$ and $BiNiO_3$.

4. Reflective optical element according to claim 1, wherein the intermediate layer comprises at least one of quartz and silicon (Si).

5. Reflective optical element according to claim 1, wherein the intermediate layer is unprocessed.

6. Reflective optical element according to claim 1, wherein the intermediate layer is mechanically processed or ion beam figured.

7. Reflective optical element according to claim 1 and configured for an operating wavelength of less than 30 nm.

8. Reflective optical element according to claim 1, configured as a mirror for a microlithographic projection exposure apparatus or a mask inspection apparatus.

9. Reflective optical element according to claim 1, configured as a reticle for a microlithographic projection exposure apparatus.

10. Optical system of a microlithographic projection exposure apparatus, comprising at least one reflective optical element according to claim 1 and configured into an illumination device or a projection lens of the projection exposure apparatus.

11. Optical system of a mask inspection apparatus, comprising at least one reflective optical element according to claim 1 and configured into an illumination device or an inspection lens of the mask inspection apparatus.

12. Microlithographic projection exposure apparatus comprising an illumination device and a projection lens, wherein the projection exposure apparatus comprises a reflective optical element according to claim 1 configured into the illumination device or the projection lens.

13. Mask inspection apparatus comprising an illumination device and an inspection lens, wherein the mask inspection apparatus comprises a reflective optical element according to claim 1 configured into the illumination device or the inspection lens.

14. Reflective optical element having an optically effective surface and comprising:
an element substrate;
a reflection layer system;
at least one deformation reduction layer which, upon the optically effective surface being irradiated with electromagnetic radiation, reduces a maximum deformation level of the reflection layer system in comparison with an analogous construction of a reflective optical element without the deformation reduction layer; and an intermediate layer arranged between the reflection layer system and the deformation reduction layer and configured to block transfer of surface roughnesses to the reflection layer system, wherein an effective volume change $\Delta V_{\mathit{eff}}$ of an arrangement comprising the reflection layer system and the deformation reduction layer that results from a heating of the optically effective surface by a predetermined temperature difference is a maximum of 90% of a volume change $V_1$ of the reflection layer system alone that results from the heating.

15. Reflective optical element according to claim 14, wherein the effective volume change $\Delta V_{\mathit{eff}}$ of the arrangement is a maximum of 90% of the volume change $V_1$ for a heating of the optically effective surface (by a temperature difference of at least 1K.

16. Reflective optical element having an optically effective surface and comprising:
    an element substrate;
    a reflection layer system; and
    at least one deformation reduction layer which, upon the optically effective surface being irradiated with electromagnetic radiation, reduces a maximum deformation level of the reflection layer system in comparison with an analogous construction of a reflective optical element without the deformation reduction layer;
    wherein the at least one deformation reduction layer comprises a heat distribution layer at a location facing the element substrate, and wherein the heat distribution layer has a thermal conductivity that is greater than a thermal conductivity of the element substrate alone.

17. Reflective optical element according to claim 16, wherein the heat distribution layer has a thermal conductivity of at least 100 W/mK.

18. Reflective optical element according to claim 16, wherein the heat distribution layer comprises at least one material selected from the group consisting essentially of graphite, aluminium (Al), silver (Ag), gold (Au), copper (Cu) and $ZrW_2O_8$.

19. Reflective optical element according to claim 16, wherein a heat insulation layer configured to delay entry of heat into the element substrate is arranged between the element substrate and one of the reflection layer system and the deformation reduction layer.

20. Reflective optical element according to claim 19, wherein the heat insulation layer comprises quartz.

21. Reflective optical element according to claim 16, further comprising:
    an intermediate layer arranged between the reflection layer system and the deformation reduction layer and configured to block transfer of surface roughnesses to the reflection layer system.

* * * * *